United States Patent
Voix et al.

(10) Patent No.: US 9,107,772 B2
(45) Date of Patent: Aug. 18, 2015

(54) SETTABLE COMPOUND DELIVERY DEVICE AND SYSTEM FOR INFLATABLE IN-EAR DEVICE

(75) Inventors: Jérémie Voix, Montreal (CA); Michael Maloney, Caledon (CA); Michael C. Turcot, Montreal (CA)

(73) Assignee: SONOMAX TECHNOLOGIES INC.

( * ) Notice: Subject to any disclaimer, the term of this patent is extended or adjusted under 35 U.S.C. 154(b) by 557 days.

(21) Appl. No.: 12/923,698

(22) Filed: Oct. 5, 2010

(65) Prior Publication Data

US 2011/0079229 A1   Apr. 7, 2011

Related U.S. Application Data

(60) Provisional application No. 61/272,535, filed on Oct. 5, 2009, provisional application No. 61/282,213, filed on Dec. 31, 2009.

(51) Int. Cl.
| | |
|---|---|
| A61F 11/10 | (2006.01) |
| B29C 33/40 | (2006.01) |
| H04R 25/00 | (2006.01) |
| H04R 1/10 | (2006.01) |

(52) U.S. Cl.
CPC .............. *A61F 11/10* (2013.01); *H04R 25/656* (2013.01); *B29C 33/405* (2013.01); *H04R 1/1058* (2013.01); *H04R 25/652* (2013.01); *H04R 25/658* (2013.01); *H04R 2225/023* (2013.01); *H04R 2225/025* (2013.01)

(58) Field of Classification Search
CPC .............. B29C 33/405; H04R 25/652; H04R 2225/025; H04R 1/1058; H04R 25/656; H04R 2225/023; H04R 25/658; A61F 11/10
USPC .............. 425/2, 89, 389, 203, 205, 206, 207, 425/145, 146, 557, 560, 562, 567, 573; 249/55, 61, 65, 141, 144, 153, 155, 249/179, 183
See application file for complete search history.

(56) References Cited

U.S. PATENT DOCUMENTS

| | | | | |
|---|---|---|---|---|
| 3,602,654 | A | * | 8/1971 | Victoreen .................... 181/135 |
| 3,788,337 | A | * | 1/1974 | Breer ............................ 521/170 |
| 4,015,602 | A | | 4/1977 | Nelson et al. |
| 4,218,203 | A | * | 8/1980 | Tilgner ........................ 425/110 |
| 4,381,272 | A | * | 4/1983 | Ehritt .......................... 264/40.3 |
| 4,442,070 | A | * | 4/1984 | Proksa et al. ................ 422/133 |
| 4,716,985 | A | * | 1/1988 | Haertl ........................... 181/130 |
| 4,800,636 | A | * | 1/1989 | Topholm .................... 29/896.21 |
| 4,871,502 | A | * | 10/1989 | LeBisch et al. ............... 264/222 |
| 5,006,055 | A | | 4/1991 | Lebisch et al. |
| 5,135,721 | A | * | 8/1992 | Richard ........................ 422/111 |

(Continued)

*Primary Examiner* — Seyed Masoud Malekzadeh
(74) *Attorney, Agent, or Firm* — Equinox IP; Franz Bonsang

(57) ABSTRACT

A method and apparatus for filling an expandable in-ear device having in-flow and out-flow canals including a plurality of chambers with elastic membranes in which the components of a settable polymer are held under high relative pressure. The component chambers are connected to a common mixing element which mixes the components before they are applied to the in-flow canal of an in-ear device. A sealed relief chamber is connected to the out-flow canal of the in-ear device and receives excessive mixed compound as it exits the in-ear device. The relief chamber is in contact with the elastic membranes of the component chambers such that when the elastic membranes contract the pressure in the relief chamber decreases, maintaining the pressure within a pre-determined pressure range.

9 Claims, 6 Drawing Sheets

(56) References Cited

U.S. PATENT DOCUMENTS

| | | | |
|---|---|---|---|
| 5,321,757 A * | 6/1994 | Woodfill, Jr. | 381/312 |
| 5,333,622 A * | 8/1994 | Casali et al. | 128/864 |
| 5,879,605 A * | 3/1999 | David | 264/223 |
| 5,885,509 A * | 3/1999 | Kristinsson | 264/314 |
| 6,339,648 B1 | 1/2002 | McIntosh et al. | |
| 6,354,990 B1 * | 3/2002 | Juneau et al. | 600/25 |
| 6,432,247 B1 * | 8/2002 | Juneau et al. | 156/245 |
| 6,438,244 B1 * | 8/2002 | Juneau et al. | 381/322 |
| 6,473,512 B1 * | 10/2002 | Juneau et al. | 381/328 |
| 6,687,377 B2 | 2/2004 | Voix et al. | |
| 6,695,943 B2 * | 2/2004 | Juneau et al. | 156/245 |
| 6,728,383 B1 * | 4/2004 | Juneau et al. | 381/322 |
| 6,754,357 B2 | 6/2004 | McIntosh et al. | |
| 6,761,789 B2 * | 7/2004 | Juneau et al. | 156/245 |
| 7,217,335 B2 * | 5/2007 | Juneau et al. | 156/245 |
| 7,478,702 B2 * | 1/2009 | Berg et al. | 181/135 |
| 7,688,983 B2 | 3/2010 | Voix et al. | |
| 7,934,916 B2 * | 5/2011 | Smith et al. | 425/2 |
| 2002/0076057 A1 | 6/2002 | Voix et al. | |
| 2004/0137098 A1 * | 7/2004 | Karason | 425/2 |
| 2005/0123146 A1 | 6/2005 | Voix et al. | |
| 2005/0136146 A1 * | 6/2005 | Pham | 425/129.1 |
| 2009/0095767 A1 | 4/2009 | Smith et al. | |
| 2009/0131939 A1 * | 5/2009 | Ahrens et al. | 606/80 |
| 2009/0184438 A1 * | 7/2009 | Buzzi | 264/254 |
| 2011/0291320 A1 * | 12/2011 | Oquist | 264/222 |
| 2013/0010993 A1 * | 1/2013 | Gebert et al. | 381/328 |

* cited by examiner

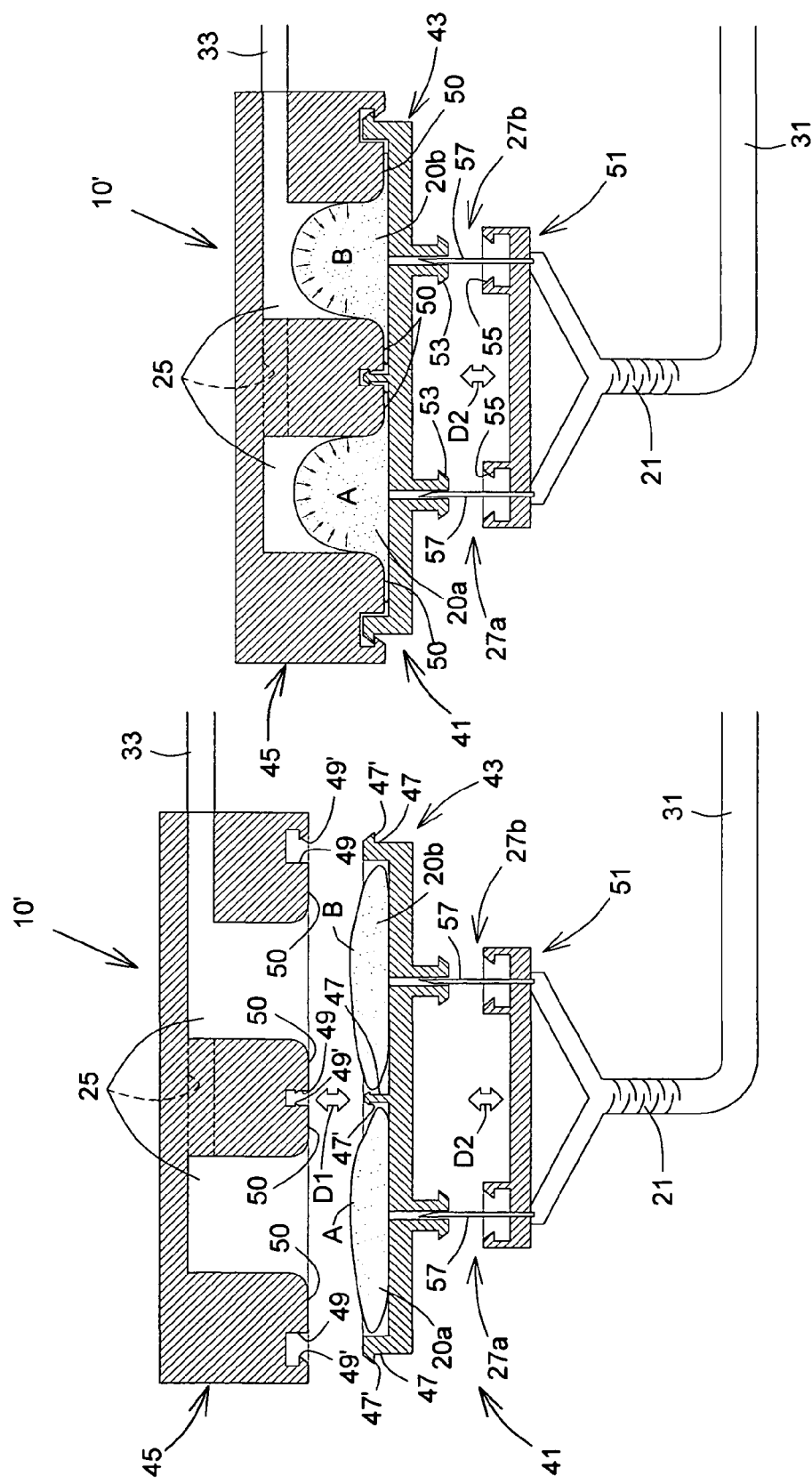

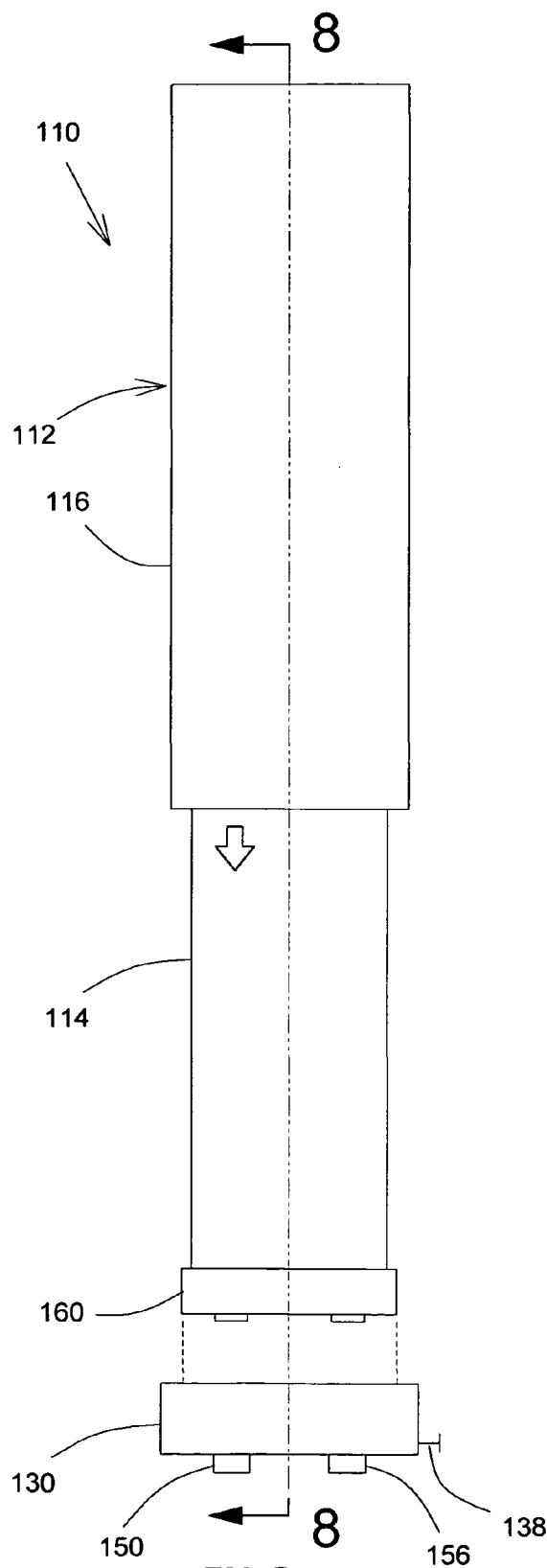
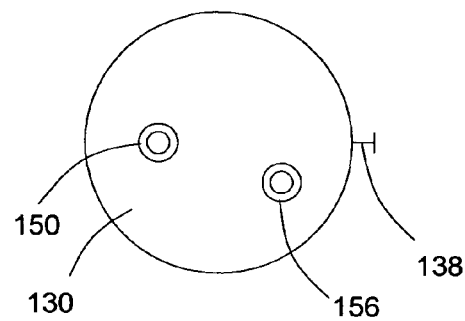
FIG.6
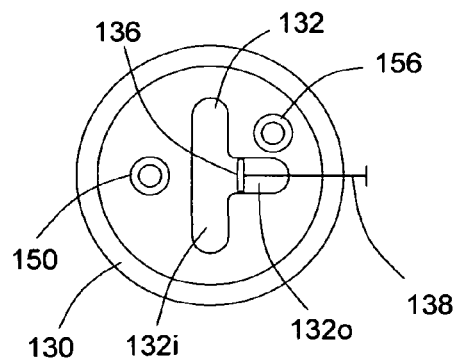
FIG.7
FIG.5

SETTABLE COMPOUND DELIVERY DEVICE AND SYSTEM FOR INFLATABLE IN-EAR DEVICE

CROSS REFERENCE TO RELATED APPLICATIONS

Benefit of U.S. Provisional Application for Patent Ser. No. 61/272,535 filed on Oct. 5, 2009, and of U.S. Provisional Application for Patent Ser. No. 61/282,213 filed on Dec. 31, 2009, both of which being incorporated herein by reference, is hereby claimed.

FIELD OF THE INVENTION

This invention relates to in-ear devices, such as intra-aural hearing protectors (earplugs), earphones, or hearing-aide devices, which are inflatable to provide proper fit within the ear canal and particularly to methods and apparatus for injecting a settable compound into the in-ear device.

BACKGROUND OF THE INVENTION

The term in-ear device includes active as well as passive devices in which all or at least a portion of the device is inserted into the ear canal of the user. The devices may include means for amplification or suppression of sound. Such devices are described in U.S. Pat. Nos. 6,754,357 and 6,339,648 (both of which are herein incorporated in their entirety) in which a rigid or semi-rigid central core component is provided with an expandable sheath over the innermost portion of the device.

The sheath, typically made of a silicone polymer material or the like, has hydrodynamic properties of a quasi-isobaric inflation process which maintains a substantially constant pressure (P1) when inflated without external constraints (similarly to an inflatable balloon), which could typically be in the order of about 0.8 psig (about 5.5 kPa relative pressure). However, when constrained within the ear canal, the internal pressure rises and causes the in-ear device to overinflate and may injure or cause discomfort to the wearer of the device (at a pressure above a comfort-limit ear canal pressure level P2) when a settable compound is injected between the core and the sheath through an injection channel, which is in the order of about 2.0 psig (about 14 kPa relative pressure).

In the prior art, although the injection pressure was attempted to be controlled through human intervention, the pressure inside the in-ear device was difficult to control and monitor, as exemplified in U.S. Pat. No. 6,687,377 and in U.S. patent application No. 2005-0123146A1 tentatively try to solve that problem of limiting the maximum pressure level by assessing in situ the acoustic attenuation of the in-ear device during the inflation mode. Furthermore, such a process required a person duly trained to inject the settable compound, which is relatively expensive in addition to the fact that an appointment may be required.

In areas of application in the industry, it is important to obtain proper fitment for achieving consistent results in both hearing aid and hearing protection applications.

Accordingly, there is a need for an improved settable compound delivery system or apparatus for an inflatable in-ear device.

BRIEF SUMMARY OF THE INVENTION

Accordingly, as a general object the invention concerns an improved settable compound delivery system for injecting the compound into an inflatable in-ear device. The compound is typically a two-part silicone (could be three-part or other settable material, etc.), automatically mixed with a mixing element, optionally stirred (via the mixing element), and delivered at a controlled and predetermined (but not necessarily constant) flow rate into the inflatable in-ear device.

An advantage of this invention is that it provides a settable compound injection system for in-ear devices in which accurate control of the injected amount is achieved, through control of the injection pressure.

Another advantage of this invention is that it provides a compact unitary system for providing customized installation of an in-ear device.

A further advantage of this invention is that the settable compound delivery system can be used and activated by the user himself, following a step-by-step sequence of instructions.

According to an aspect of the present invention, there is provided an apparatus for injecting a settable compound into an in-ear device having an inflow canal and an outflow canal both coupled to an expandable chamber for fitment into a wearer's ear canal, the apparatus comprising:

a plurality of pressurizable component chambers for containing components of a settable compound, each said component chamber being pressurizable by a pressure mechanism;

a mixing element connected to all of the component chambers via a respective valve; and a first tube for connecting the mixing element to the in-flow canal of an in-ear device.

In one embodiment, each said pressure mechanism includes a compressed air chamber fillable with compressed air and connecting to each said component chamber.

Conveniently, the apparatus further includes a cover slidably and sealably mounted on a main body and forming a closed charged air chamber therewith, said charged air chamber connecting to said compressed air chamber whereby displacement of said cover relative to said main body displaces and compresses form said charged air chamber to said compressed air chamber.

Typically, each said component chamber includes a respective piston for displacing the respective compound component therein when in contact with the compressed air from the compressed air chamber.

Conveniently, the main body includes an activation piston movably mounted therein and connecting to said charger air chamber and said compressed air chamber, said respective valve being a plug connecting to said activation piston and being operable by displacement thereof.

In one embodiment, the apparatus further includes at least one pressurizable relief chamber connecting to a sealed space located between said cover and said main body, and a second tube for connecting the out-flow canal of an in-ear device to the relief chamber, a volume of said sealed space enlarging during displacement of said cover relative to said main body.

Typically, the apparatus further includes an injection unlocking mechanism to selectively connect the compressed air chamber to the plurality of component chambers.

In one embodiment, each said pressure mechanism includes an elastic membrane bounding at least a portion of respective said component chamber.

Typically, the apparatus includes at least one pressurizable relief chamber in contact with the elastic membranes of all of the components chambers, and a second tube for connecting the out-flow canal of an in-ear device to the relief chamber.

According to another aspect of the present invention, there is provided a method of injecting a multiple component settable compound into an in-ear device having an inflow and an outflow canal coupled to an expandable chamber for fitment into a wearer's ear canal using the above-described apparatus, the method comprising the steps of:

provided a plurality of pressurizable component chambers, at least one said chamber for each component of the multiple component settable compound;

coupling a mixing element to the in-flow canal of an in-ear device;

pressurizing each of a plurality of component chambers to a first pressure being great enough for forcing the respective component out of the chamber into and through the expandable chamber of an in-ear device; and simultaneously allowing flowing of all of the multiple components from the respective said component chambers to the mixing element for passing all of the multiple components through the mixing element to mix the components, and passing the mixed components into and at least partially through the in-ear device to expand the expandable chamber to conform to the surface of the wearer's ear canal.

Conveniently, the step of coupling a mixing element further includes coupling a relief chamber to the out-flow canal of the in-ear device; the method further includes the step of partially vacuuming said relief chamber; and the step of simultaneously allowing flowing of all the multiple components further includes simultaneously allowing an excess amount of mixed settable compound to exit from the expandable chamber of the in-ear device through the out-flow canal thereof.

In one embodiment, the step of pressurizing each component chamber includes tensioning a corresponding elastic membrane bounding at least a portion of respective said component chamber, and the method further includes providing a relief chamber in communication with the elastic membranes of the component chambers, and coupling the outflow canal of the in-ear device to the relief chamber.

Conveniently, the step of simultaneously allowing flowing of all of the multiple components includes simultaneously opening a plurality of valves respectively connecting the plurality of component chambers to the mixing element for passing all of the multiple components through the mixing element to mix the components, and passing the mixed components into and at least partially through the in-ear device to expand the expandable chamber to conform to the surface of the wearer's ear canal.

In one embodiment, the step of pressurizing each component chamber includes compressing air into a compressed air chamber being connectable to said component chambers, and opening mixing valves downstream of corresponding said component chambers.

Conveniently, the step of simultaneously allowing flowing of all of the multiple components includes simultaneously pushing on the plurality of pistons located inside a respective said component chamber to simultaneously force all of the multiple components to flow out from respective said component chambers to the mixing element for passing all of the multiple components through the mixing element to mix the components, and passing the mixed components into and at least partially through the in-ear device to expand the expandable chamber to conform to the surface of the wearer's ear canal.

These and other advantages and objects will be apparent in view of the following detailed description in connection with the accompanying drawings.

BRIEF DESCRIPTION OF THE DRAWINGS

Further aspects and advantages of the present invention will become better understood with reference to the description in association with the following figures, in which similar references used in different figures denote similar components, wherein:

FIGS. 2 and 3 are schematic views of a second embodiment of a settable compound delivery apparatus in accordance with the present invention showing the injector assembly before and after activation thereof, respectively, induced by the snapping assembly of the two upper parts to one another followed by the snapping of the lower part therewith;

FIG. 5 is a schematic exploded front elevation view of a fourth embodiment of a settable compound delivery apparatus in accordance with the present invention, in an extended configuration;

FIGS. 6 and 7 are bottom and top plan views of the bottom cap of the embodiment of FIG. 5;

DETAILED DESCRIPTION OF THE PREFERRED EMBODIMENTS

Figure 1:
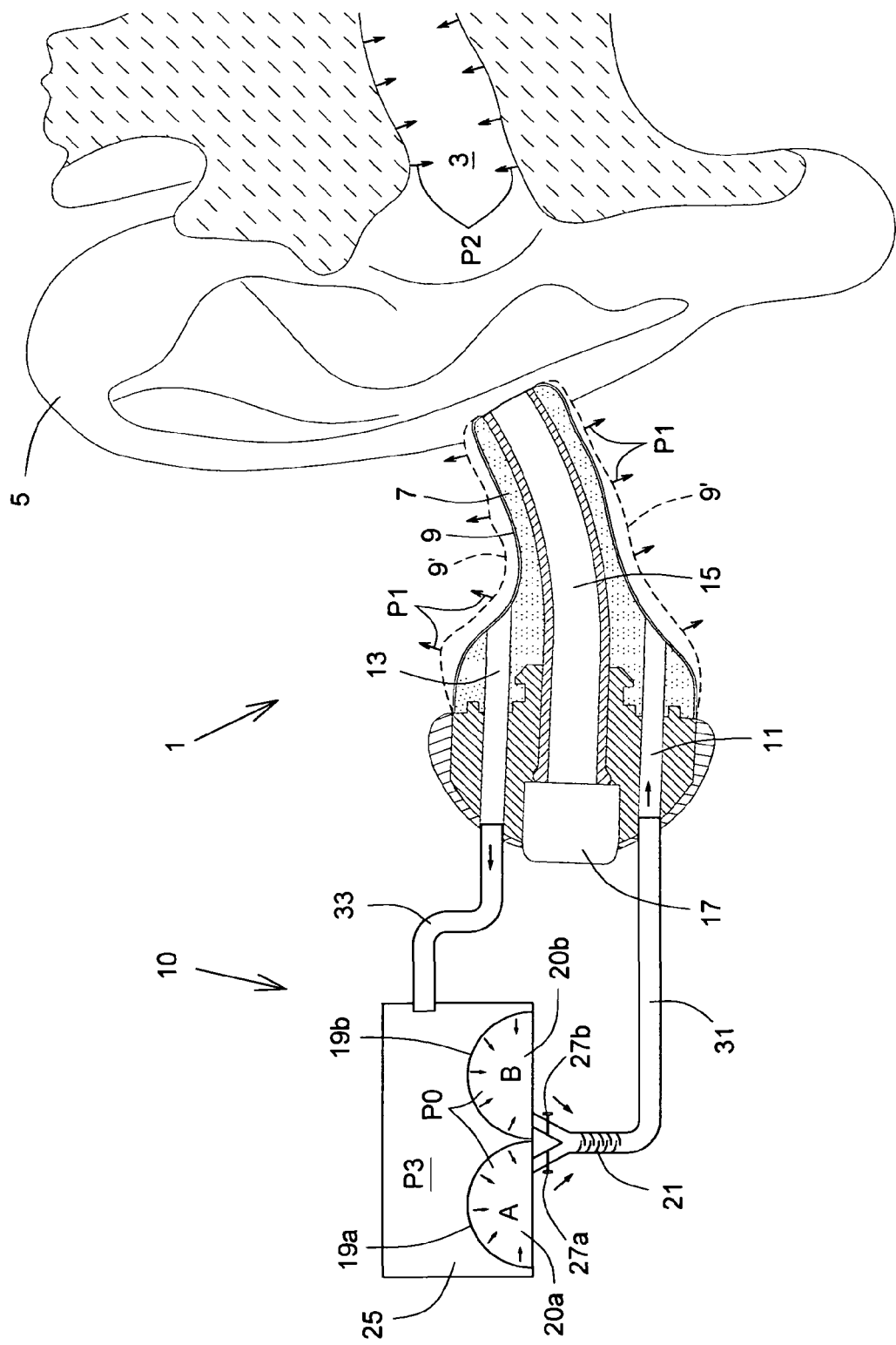
FIG. 1 is a schematic view of a settable compound delivery apparatus and system in accordance with an embodiment of the present invention showing the coupling of the settable compound mixing apparatus coupled to the in-ear device before insertion into an ear canal.

The apparatus or system shown in the drawings and described below are examples which embody the invention. It should be noted that the scope of the invention is defined by the accompanying claims and not necessarily by specific features of the exemplary embodiments.

Referring to FIG. 1 all of the elements of the system of the invention are shown as follows. In-ear device is shown adjacent to the ear canal 3 of ear 5. In-ear device 1 comprises a core 7 which is formed by being injection-molded from a suitable material. Core 7 has its narrow end covered by a sheath 9 formed of a material suitable for contact with the skin of the inside of the ear canal 3. Included in core 7 are an in-flow canal 11, an out-flow canal 13 and a sound bore 15. Sound bore 15 contains active or passive sound modifying unit 17. An example of manufacture and details of the in-ear device 1 is described in more detail in U.S. Pat. No. 6,339,648 B1.

In accordance with the invention operation of the system will now be described. It will be understood that in operation the in-ear device 1 will be inserted into the ear canal 3 of the user.

Accordingly, the delivery system 10 of the invention includes a settable compound delivery system for injecting the compound into the in-ear device, inside the space between the core 7 and the sheath 9. The injected compound is typically a two-part silicone component A and B, but also could be three-part or more. Components A and B are stored within respective pressurizable component chambers 20a, 20b with corresponding pressure mechanism as in the form of elastic membranes 19a and 19b and are automatically mixed in the proper ratio (equal or not) with a mixing element 21 or optionally stirred via a different mixing element, not shown, and delivered into the inflatable in-ear device 1 through in-flow tube 31 coupled to in-flow canal 11. Each component is typically located inside the pressurized chamber 20a, 20b and maintained therein with closed valves 27a and 27b, the chamber pressure being essentially the same for all parts. Alternatively, the pressure P0 could be generated by other mechanisms such as a spring and piston assembly or the like.

Upon simultaneous triggering of the closed mixing valves 27a and 27b (via push button or the like—not specifically shown in FIG. 1), the component parts of the settable compound are mixed together and delivered into the in-ear device 1 until all of the material has been delivered expanding the sheath 9 to conform to the surface of the wearer's ear canal 3 as shown by the expanded sheath 9' in dashed line.

Typically, the pressurized chambers 20a and 20b are separated from a lower pressure (such as ambient pressure) relief chamber 25, that is connected to the out-flow canal 13 of the in-ear device, typically via a flexible (elastic) tube 33, such that when the compound parts exit the pressurized chambers 20a 20b, a relative vacuum is created in the relief chamber 25 on the opposite side of the membranes which allows un-required excess amount of settable compound to flow outside from the in-ear device 3 into relief chamber 25 and ensure that no air is entrapped inside sheath 9. In such a case, the system ensures that the pressure inside the relief chamber is always maintained at a predetermined pressure level P3, between P1 (quasi-isobaric inflation pressure of sheath) and P2 (comfort-limit ear canal pressure level) delimiting a pre-determined pressure range.

In some embodiments, the use of flexible membranes 19a and 19b inside of relief chamber 25 allow the delivery system to be contained in a unitary easily transportable unit.

More specifically, in FIGS. 2 and 3, there is shown a second embodiment of a settable compound delivery apparatus 10' in which the components A, B are located inside respective elastic chambers 20a, 20b positioned onto a lower section 43 of a main body 41 of the apparatus 10' and adapted to be connected onto an upper section 45. Upon connection of the lower and upper sections via lower wall members 47 engaging respective guide channels 49, as illustrated by arrow D1 in FIG. 2, the chambers 20a, 20b are squeezed by the respective thicker upper walls 50 of upper section 45 thus increasing the internal pressure thereof, as shown in FIG. 3. The squeezed chambers 20a, 20b keep their internal pressure since the lower walls 47 remain snapped inside their respective channel 49 under the action of wall lips 47' engaging corresponding notches 49' inside the channels 49.

Furthermore, just after the lower and upper sections 43, 45 are snapped together, a needle section 51 is similarly snapped onto the lower section 43, via similar attachment lips 53 of the lower section 43 snappingly engaging corresponding notches 55 of the needle section 51, as illustrated by arrow D2 in FIGS. 2 and 3. Upon snapping, hollow needles 57 of the needle sections 51 simultaneously perforate the wall of the corresponding pressurized chamber 20a, 20b to allow the flow of the different compound components A, B located therein through the needles 57 toward the mixing element 21 and the in-flow tube 31.

It is noted that guiding structures needed to ensure the proper sliding alignment between the lower and upper sections 43, 45 and between the lower section 43 and the needle section 51 are not shown. Furthermore, a synchronizing mechanism (not shown) could be used to ensure the proper sequence of both snapping actions, with both being performed successively during a common external action.

Optionally, there could be a respective relief chamber associated with each pressure chamber and all the relief chamber could be connected to each other to ensure uniform pressure within the relief chambers.

Typically, the size (volume) of the overflow relief chamber should be sufficient to ensure the entirety of the injected settable compound could be received therein, such that during injection, the whole quantity of the compound can be injected without risks for the wearer, while ensuring that the pressure inside the space between the sheath 9 and the core 7 is maintained within the pre-determined pressure range.

Figure 4:
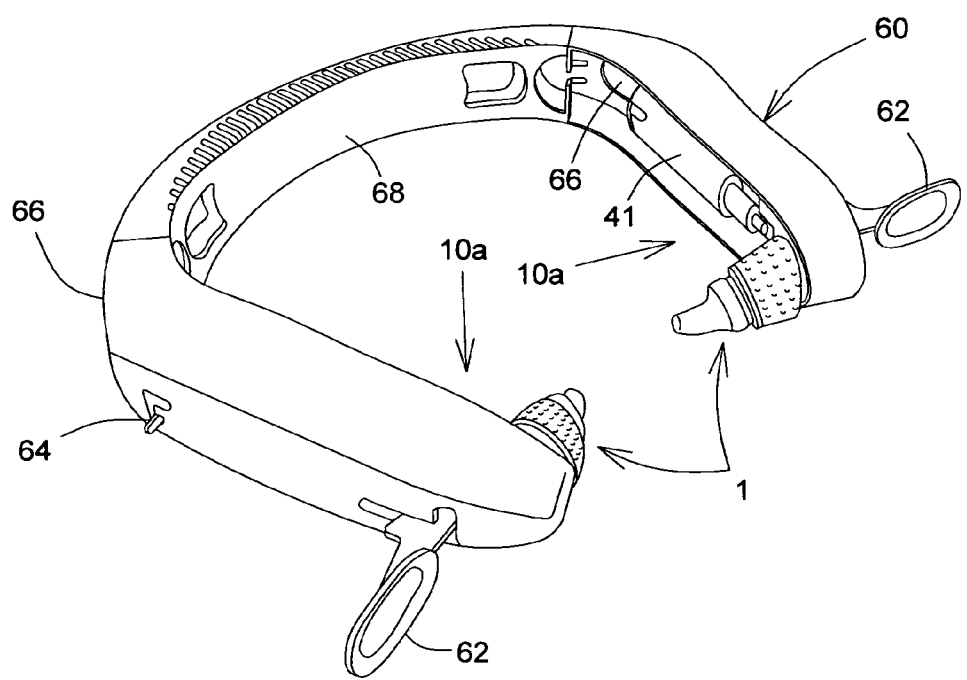
FIG. 4 is a schematic perspective view of a headband of a settable compound delivery system for inflatable in-ear devices in accordance with a third embodiment of the present invention.

With reference to FIG. 4, there is shown a third embodiment of a settable compound delivery system 10a for inflatable in-ear devices 1 located inside of a generally rigid adjustable headband support structure device 60. The headband device 60 carries all the equipment required for a self injecting settable compound delivery system 10a and is adapted to removably receive the left and right inflatable in-ear devices 1 thereon such that the user can take the in-ear devices off after fitting injection thereof. Before activating the self-injection system 10a, the user properly adjust the position of the headband device 60 to ensure that the two un-inflated (or virgin) in-ear device 1 are properly positioned within the respective ear (not shown), including the ear canal (not shown).

The third embodiment of settable compound delivery system 10a includes, for each in-ear device 1, a pump mechanism, shown here in the form of a hinged lever 62 biasing a compression coil spring (not shown) or the like connected to a main piston (not shown), activatable by the user to apply pressure (typically between about 20 and 40 psi) inside the different chambers or compartments of the parts A & B (may typically have more than one compartment for each part, all positioned as a plurality parallel cylinders equally circumferentially spread in alternating manner about the axis of the main body 41 of the pump mechanism) of the settable compound, via the main piston, prior to the injection thereof inside the in-ear device. An unlocking injection mechanism, typically one for each pump mechanism and shown here in the form of a rotating tab 64, allows the user to unlock the activation (injection release) mechanism, shown here as a push button 66 (similar to the needle section 51) that essentially simultaneously perforates the walls of the different compartments for flowing of the settable compound, to allow the user to start the self-injection delivery of the settable compound into the in-ear device. The unlocking injection mechanism 64 typically prevents the user from inadvertently starting the activation mechanism (pushing on the corresponding button 66) before the corresponding in-ear device 1 is properly positioned into the ear, and before the pump mechanism 62 has been operated. Although not illustrated, the operation of the pump mechanism could also include a release mechanism (not shown) that would release and allow operation of the unlocking injection mechanism 64 upon pressurizing the settable compound inside the compartments via the lever 62.

With reference to FIGS. 5 to 12, there is shown a fourth embodiment of a settable compound delivery apparatus 110 for inflatable in-ear devices 1, in which the pump mechanism includes an air pump 112, typically actuatable by the user and part of the pressure mechanism, formed of a typically cylindrical main body 114 with an outer top cover 116 axially slidably and sealably mounted thereon, and defining a closed charged air chamber 118 therewith. The top cover 116 is slidable on the main body 114 from an extended configuration (shown in FIGS. 5, 8 and 9) in which the air chamber 118 is filled with air at generally ambient pressure to a retracted configuration (shown in FIG. 11) in which the air is compressed inside a small area 120 above an activation piston 122 and inside a compressed air cylindrical chamber 124 in fluid communication with the small area 120 and axially extending along the main body 114. In order to ensure the air gets compressed, the cover 116 typically slides on two body O-rings 126 located inside respective circumferential outer grooves 128 of the main body 114.

Figure 8:
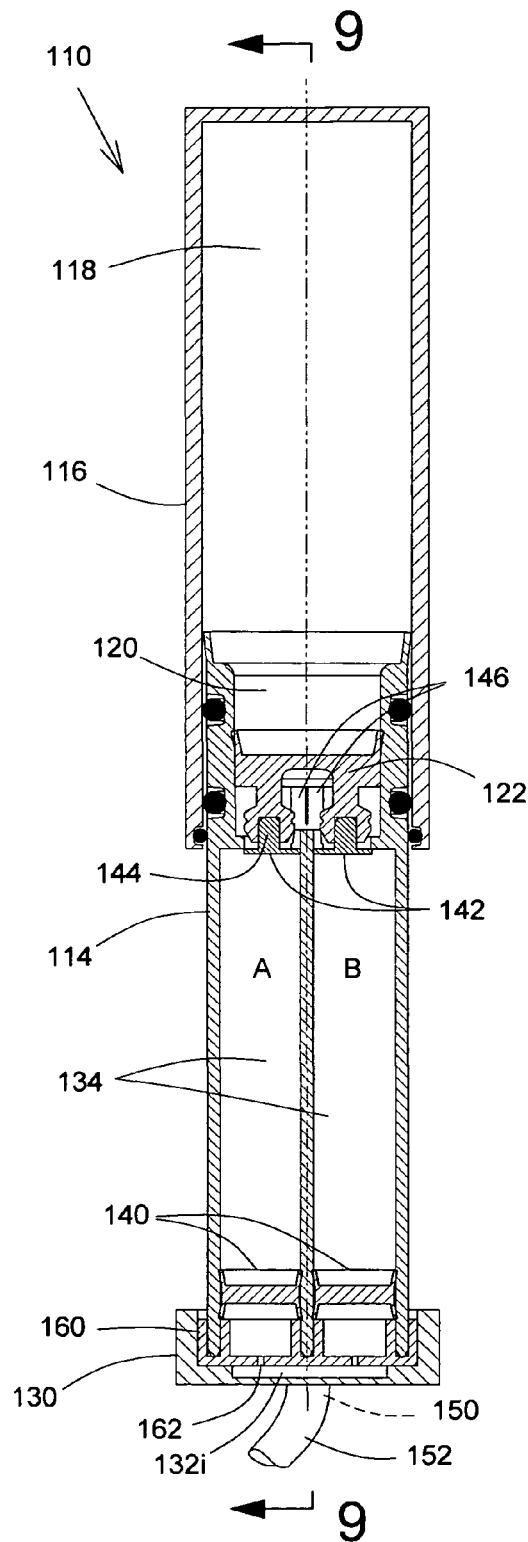
FIG. 8 is a schematic section view taken along line 8-8 of FIG. 5, showing the two component chambers in the main body.
Figure 9:
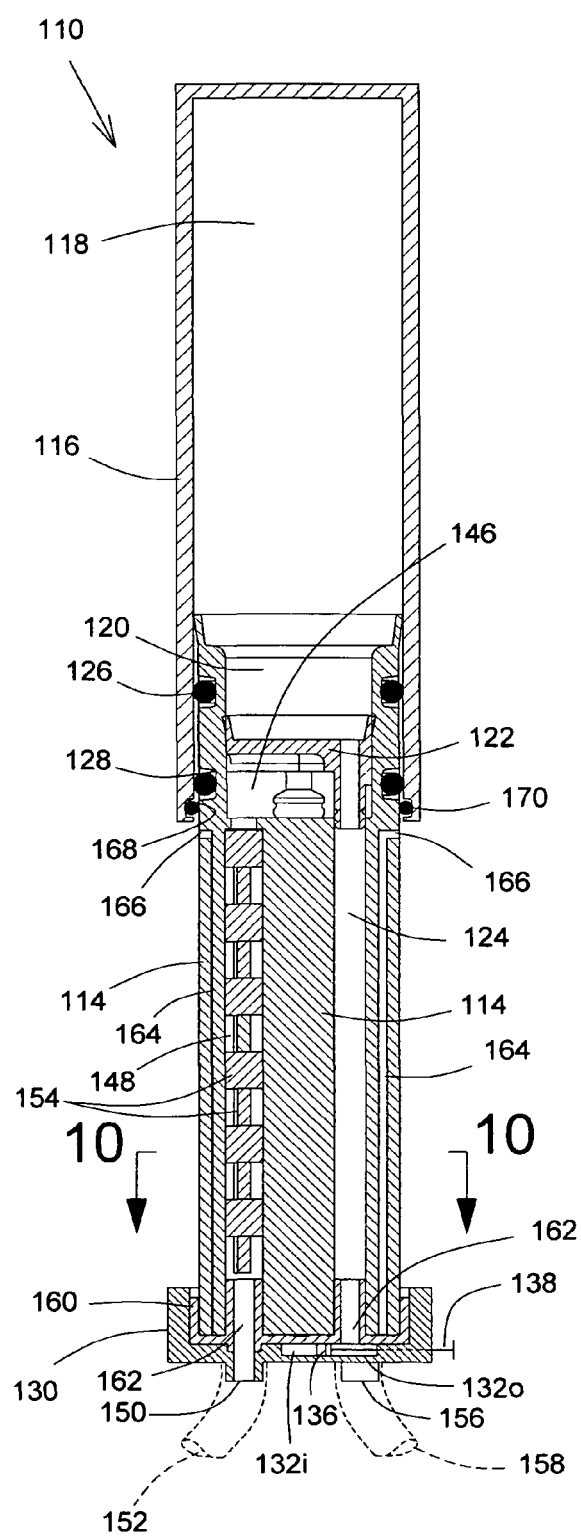
FIG. 9 is a schematic section view taken along line 9-9 of FIG. 8, showing the compressed air chamber and the mixing chamber.
Figure 10:
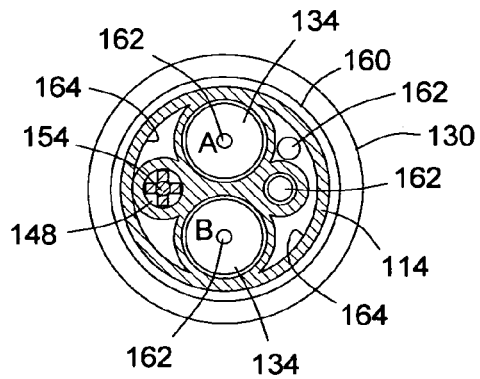
FIG. 10 is a schematic section view taken along line 10-10 of FIG. 9, showing the relative positions of the two component chambers, the compressed air chamber, the mixing chamber and the relief chamber(s)
Figure 11:
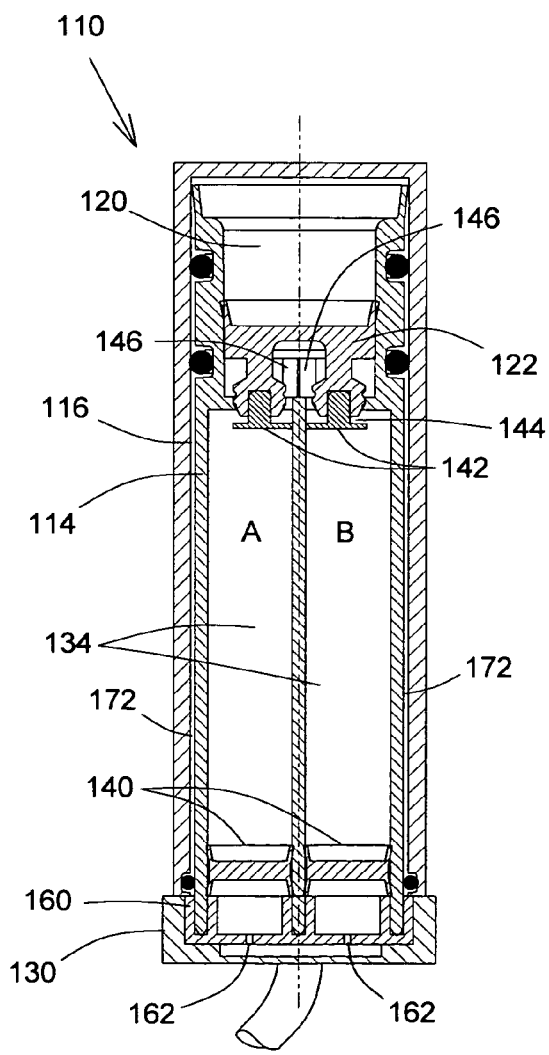
FIGS. 11 and 12 are schematic section views similar to FIG. 8, showing the top cover in a retracted configuration with the two component chambers filled with the respective component of the settable compound and emptied, respectively.

Now referring more specifically to FIGS. 7 and 9, the compressed air cylindrical chamber 124 is in fluid communication with an outer portion 132o of an internal cavity 132 of an outer bottom cap 130 sealably mounted on the lower end of the main body 114, opposite the top cover 116. An inner portion 132i of the internal cavity 132 is in fluid communication with two unpressurized (at this stage) cylindrical component chambers 134 axially extending along the main body 114 and filled with corresponding components A, B of the settable compound. The inner 132i and outer 132o portions of the internal cavity 132 are separated from one another by a breakable wall 136 breakable via an injection unlocking mechanism, schematically represented breaking pin 138 or the like (obviously, the breaking pin 138 is sealably mounted on the outer bottom cap 130 to prevent the compressed air inside the compressed air cylindrical chamber 124 and the outer portion 132o to leak outside therefrom). As shown in FIGS. 8 and 11, the two component chambers 134 are typically sealably closed at the bottom end by a respective chamber piston 140, and at the top end by a respective plug 142 (acting as a mixing valve) mounted on a shaft 144 in contact abutment with the activation piston 122. Upon compressing the air when lowering retracting the top cover 116, the activation piston slightly moves downward by simultaneously pushing the two plugs 142 inside their component chambers 134, thus leaving the top end thereof essentially opened. From this time, for a few seconds or minutes, each component remains essentially inside its respective chamber 134 in the absence of any pressure, because of its own viscosity.

Figure 12:
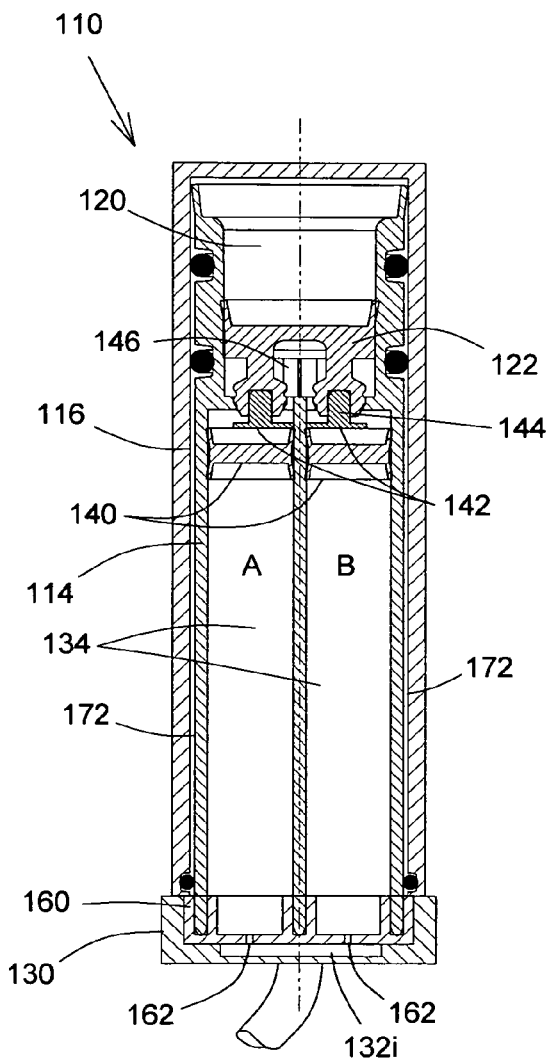

After the air is compressed inside the compressed air cylindrical chamber 124 and the outer portion 132o, the user typically pushes on the breaking pin 138 to break the wall 136 between the inner 132i and outer 132o portions of the internal cavity 132, as seen in FIG. 12, to allow the compressed air to simultaneously push on and upwardly displace the pistons 140 and ensure the components A, B are simultaneously forced outside of their respective chamber 134 into a respective component channel 146 formed inside the activation piston 122 to direct the component into a component mixing chamber 148 extending generally axially along the main body 114 and through the outer bottom cap 130 having an output spout 150 connectable to an in-flow tube 152 itself connected to the in-flow canal 11 of the core 7 of the in-ear device 1 (as shown in FIG. 1). The mixing chamber 148 typically include the mixing element 154, similar to the one 21 of FIGS. 1 to 3. In order to ease the manufacturing of the apparatus 110, an inner bottom cap 160 is sealably mounted in sandwich between the lower end of the main body 114 and the outer bottom cap 130. The inner bottom cap 160 includes openings 162 axially extending therethrough and which are extensions of the respective compressed air cylindrical chamber 124, the two component chambers 134 and the component mixing chamber 148.

The outer bottom cap 130 typically also includes an input spout 156 connectable to an out-flow tube 158 itself connected to the out-flow canal 13 of the core 7 of the in-ear device 1 (as shown in FIG. 1). The input spout 156 is in fluid communication with a relief chamber(s) 164, shown in FIGS. 9 and 10, generally axially extending along the main body 114 in between the different chambers 124, 134, 148. At the upper end of the main body 114, typically just below the top cover 116, when in the extended configuration, the relief chamber(s) 164 is in communication with the outside of the body via at least one radial hole 166. The top cover 116 typically includes an inner circumferential groove 168 adapted to receive a cover O-ring 170 therein, and located just below the two body O-rings 126. Upon sliding of the top cover 116 along the main body 114, the enlarging volume of the space 172 between the main body 114 and the top cover 116 (as shown in FIGS. 11 and 12) will create a partial vacuum therein and inside the relief chamber(s) 164 in fluid communication therewith, such that the relief chamber 164 operates similarly than the relief chamber 25 of FIGS. 1 to 3. Obviously, there is also a respective opening 162 extending through the inner bottom cover 160 to ensure the fluid communication between the input spout 156 and the relief chamber 164.

Although not shown herein, this fourth embodiment 110 could also include a include a release mechanism (not shown) that would release and allow operation of the breaking pin 138, or unlocking injection mechanism via the top cover reaching its retracted configuration and having pressurized the air cylindrical chamber 124.

While the invention has been described in terms of a plurality of embodiments, those skilled in the art will recognize that variations in detail can be made without violating the spirit of the invention.

We claim:

1. An apparatus for injecting a settable compound into an in-ear device having an inflow canal and an outflow canal both coupled to an expandable chamber for fitment into a wearer's ear canal, the apparatus comprising:
   a plurality of pressurizable component chambers for containing components of a settable compound, each said component chamber being pressurizable by a pressure mechanism at a predetermined chamber pressure level;
   a relief chamber being in contact with said pressure mechanism for being depressurizable thereby;
   a mixing element connected to all of the component chambers via a plurality of respective valves positioned therebetween, all said respective valves being simultaneously openable;
   a first tube for connecting the mixing element to the in-flow canal of an in-ear device; and
   a second tube for connecting the relief chamber to the out-flow canal of the in-ear device:
   wherein, upon simultaneous opening of each said respective valves, each of the components of the settable compound automatically flowing toward said mixing element and said first tube from respective said pressurized component chambers, with said second tube and relief chamber simultaneously allowing air entrapped into the expandable chamber of the in-ear device and excess of the settable compound to flow thereto.

2. The apparatus of claim 1, wherein each said pressure mechanism includes a compressed air chamber fillable with compressed air and connecting to each said component chamber.

3. The apparatus of claim 2, further including a cover slidably and sealably mounted on a main body and forming a closed charged air chamber therewith, said charged air chamber connecting to said compressed air chamber whereby displacement of said cover relative to said main body displaces and compresses form said charged air chamber to said compressed air chamber.

4. The apparatus of claim 3, wherein each said component chamber includes a respective piston for displacing the respective compound component therein when in contact with the compressed air from the compressed air chamber.

5. The apparatus of claim 4, wherein said main body includes an activation piston movably mounted therein and connecting to said charged air chamber and said compressed air chamber, said respective valve being a plug connecting to said activation piston and being operable by displacement thereof.

6. The apparatus of claim 3, wherein said relief chamber connecting to a sealed space located between said cover and said main body, a volume of said sealed space enlarging during displacement of said cover relative to said main body so as to depressurize said relief chamber.

7. The apparatus of claim 3, further including an injection unlocking mechanism to selectively connect the compressed air chamber to the plurality of component chambers.

8. The apparatus of claim 1, wherein each said pressure mechanism includes an elastic membrane bounding at least a portion of respective said component chamber.

9. The apparatus of claim 8, wherein said relief chamber is in contact with the elastic membranes of all of the components chambers.

* * * * *